United States Patent
Lee et al.

(10) Patent No.: US 11,110,126 B2
(45) Date of Patent: Sep. 7, 2021

(54) METHOD OF EXPANDING NK CELL AND COMPOSITION FOR CULTURING

(71) Applicant: Korea University Research and Business Foundation, Seoul (KR)

(72) Inventors: Kyung-Mi Lee, Seoul (KR); Jeongwon Sohn, Seoul (KR); Seon Ah Lim, Seoul (KR); Jang-Mi Lim, Pohang-Si (KR)

(73) Assignee: Korea University Research and Business Foundation, Seoul (KR)

( * ) Notice: Subject to any disclaimer, the term of this patent is extended or adjusted under 35 U.S.C. 154(b) by 93 days.

(21) Appl. No.: 16/281,372

(22) Filed: Feb. 21, 2019

(65) Prior Publication Data

US 2019/0183995 A1 Jun. 20, 2019

Related U.S. Application Data

(62) Division of application No. 15/204,407, filed on Jul. 7, 2016, now abandoned.

(30) Foreign Application Priority Data

Jul. 10, 2015 (KR) .................. 10-2015-0098269
Jul. 6, 2016 (KR) .................. 10-2016-0085642

(51) Int. Cl.
| | | |
|---|---|---|
| *A61K 31/4184* | (2006.01) | |
| *A61K 35/17* | (2015.01) | |
| *C12N 5/0783* | (2010.01) | |
| *A61K 35/00* | (2006.01) | |
| *A61K 35/02* | (2015.01) | |
| *A61K 35/04* | (2006.01) | |
| *A61K 39/00* | (2006.01) | |

(52) U.S. Cl.
CPC ............ *A61K 35/17* (2013.01); *C12N 5/0646* (2013.01); *A61K 2039/5158* (2013.01); *A61K 2039/585* (2013.01); *C12N 2501/998* (2013.01); *C12N 2501/999* (2013.01)

(58) Field of Classification Search
CPC .......... A61P 35/00; A61P 35/02; A61P 35/04; A61K 2039/585; A61K 2039/5158; A61K 35/17; A61K 31/4184
See application file for complete search history.

(56) References Cited

U.S. PATENT DOCUMENTS

| 6,916,833 B2 * | 7/2005 | Kim .................. A61P 35/00 514/328 |
| 8,178,727 B2 * | 5/2012 | Shibata ............... A61P 35/00 568/325 |
| 2002/0119119 A1 | 8/2002 | Hellstrand et al. |
| 2006/0093605 A1 * | 5/2006 | Campana .......... C07K 16/2866 424/145.1 |
| 2007/0006332 A1 * | 1/2007 | O'Neill ............. C07K 14/4746 800/14 |
| 2012/0149660 A1 * | 6/2012 | Liu ..................... C07D 207/16 514/63 |

OTHER PUBLICATIONS

Lindqvist et al. ("Potentiation of Natural Killer Cell Activity with Myricetin." Anticancer Research 34: 3975-3980 (2014)). (Year: 2014).*

* cited by examiner

*Primary Examiner* — Jeffrey S Lundgren
*Assistant Examiner* — Chris E Simmons
(74) *Attorney, Agent, or Firm* — Fox Rothschild LLP

(57) ABSTRACT

Provided are a method of ex-vivo culture of natural killer (NK) cells by treating the cells with a reactive oxygen species (ROS) inhibitor and/or a p53 protein inhibitor; and a composition comprising the cultured NK cells. By reducing the activity of ROS and p53 proteins during ex-vivo culture, NK cells may have achieved greater expansion efficiency without altering their anti-tumor cytotoxicity.

6 Claims, 7 Drawing Sheets

[FIG. 1]
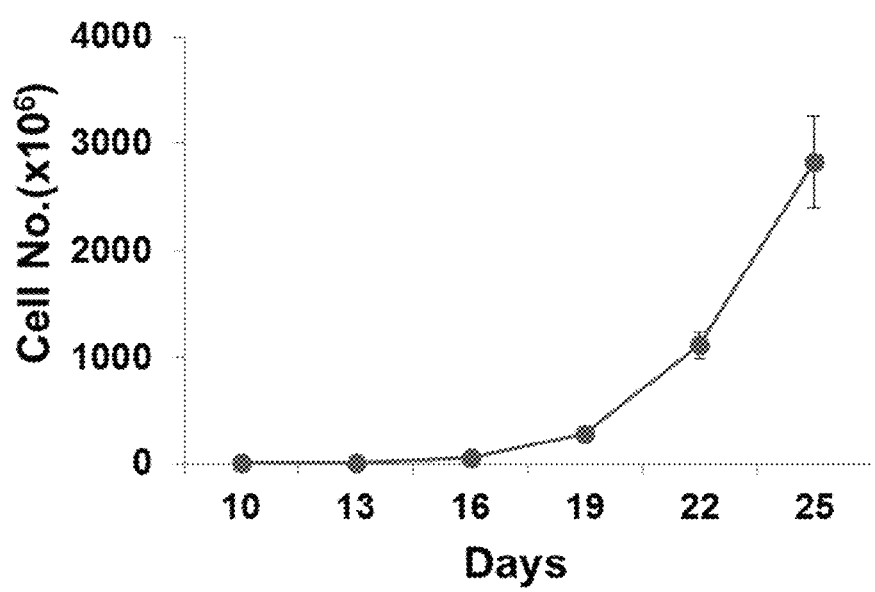

[FIG. 2]
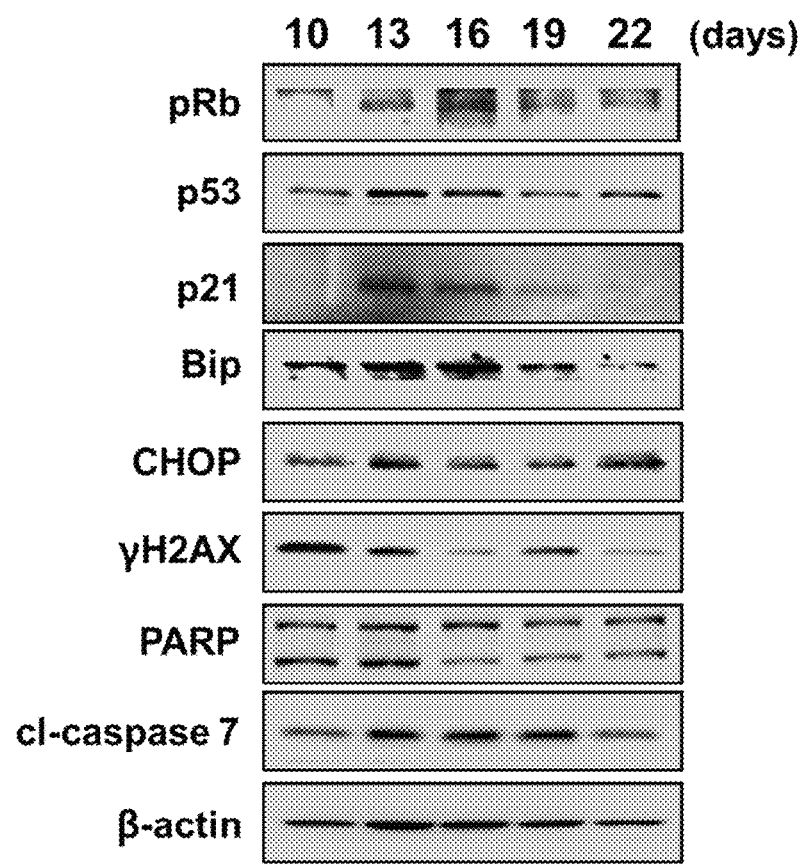

[FIG. 3]
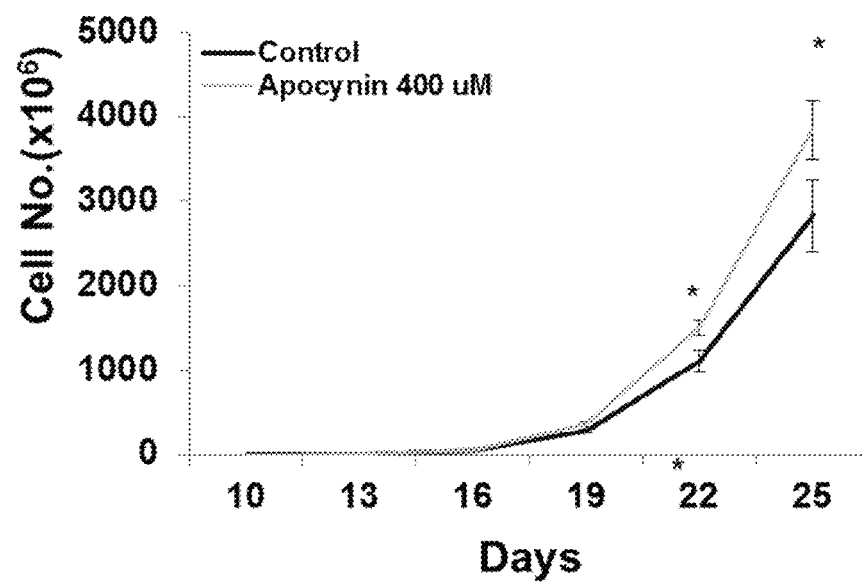
[FIG. 4]
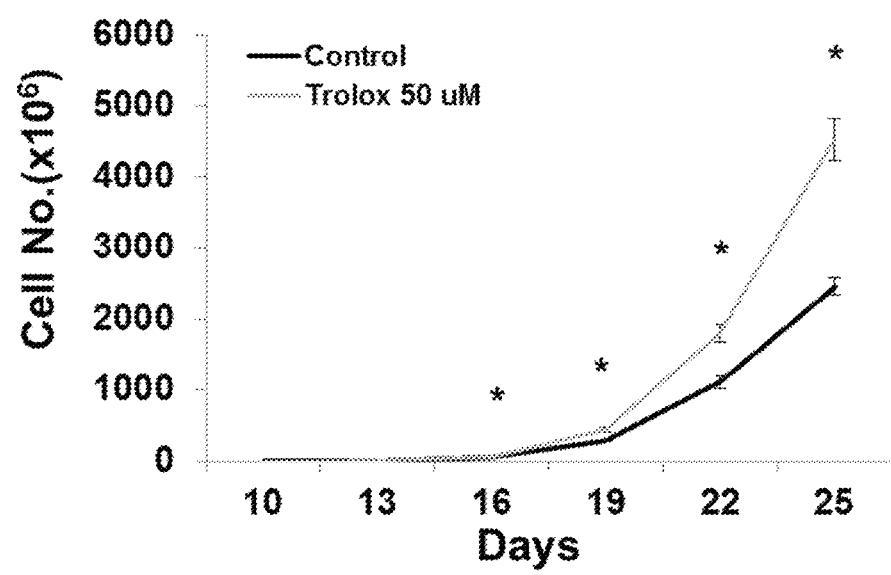

[FIG. 5]
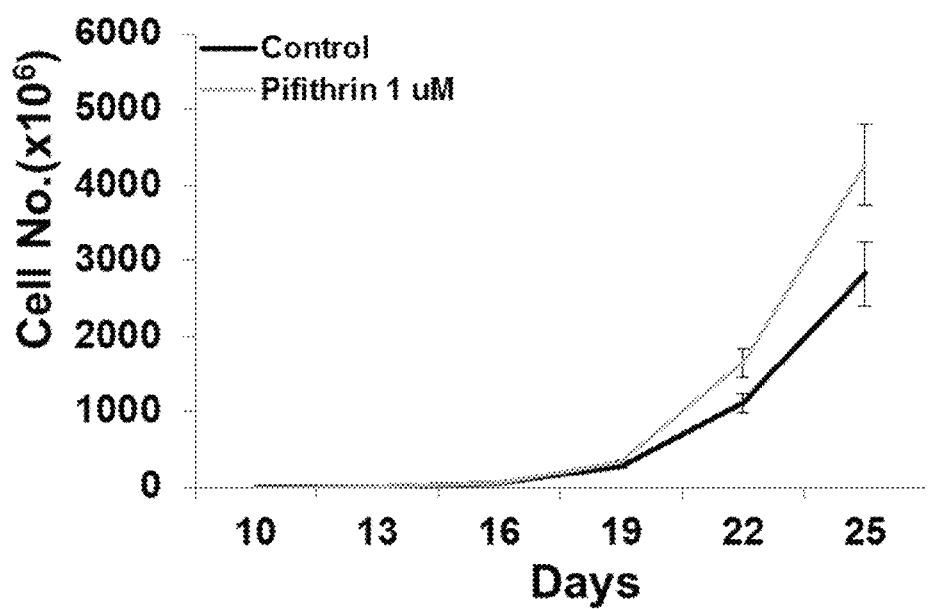
[FIG. 6]
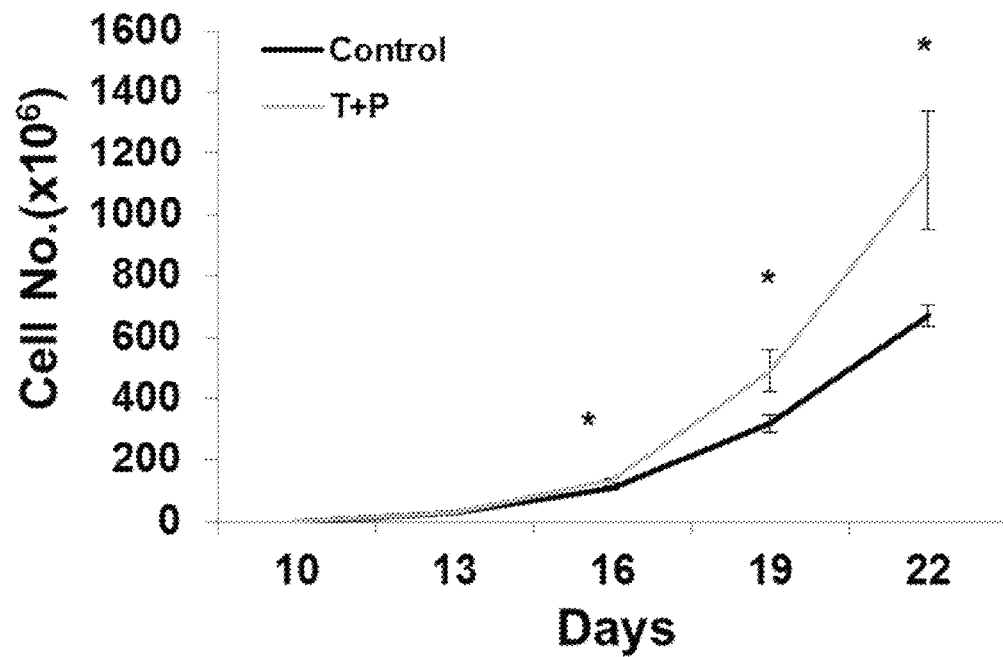

[FIG. 7]
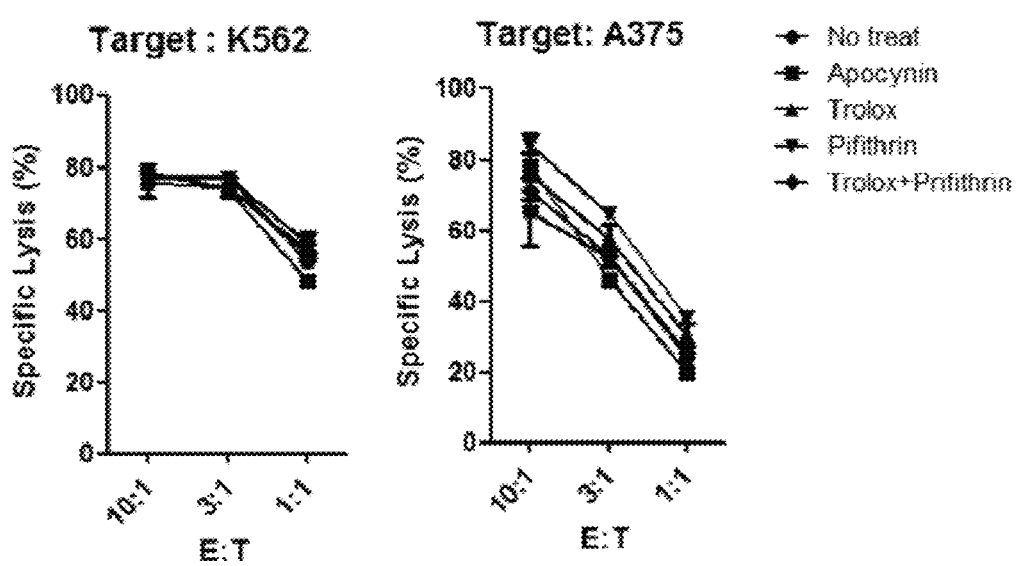

[FIG. 8]
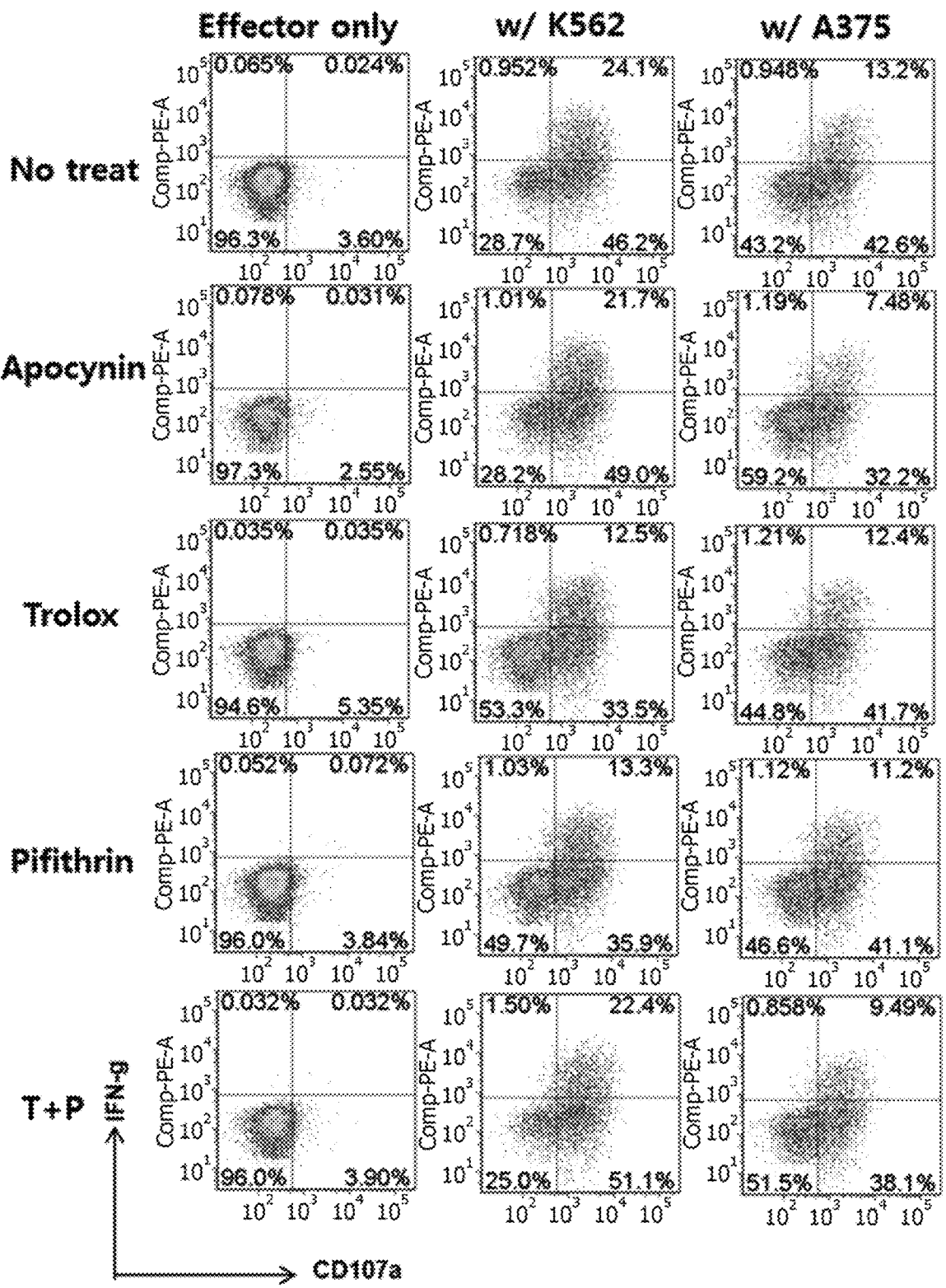

[FIG. 9]
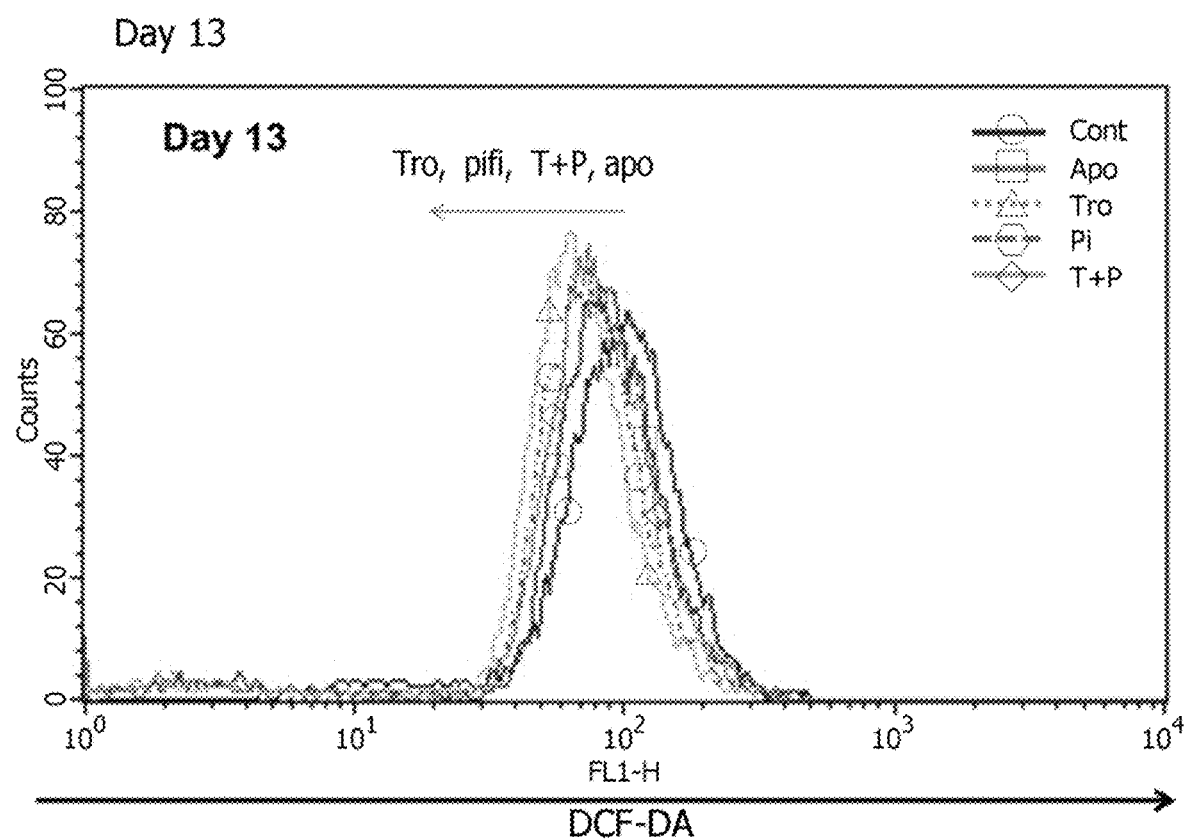

METHOD OF EXPANDING NK CELL AND COMPOSITION FOR CULTURING

CROSS-REFERENCE TO RELATED APPLICATIONS

This application is a Divisional of U.S. application Ser. No. 15/204,407, filed Jul. 7, 2016, which claims priority to and the benefit of Korean Patent Application Nos. 10-2015-0098269 filed on Jul. 10, 2015 and 10-2016-0085642, filed Jul. 6, 2016, the disclosures of which are incorporated herein by reference in their entireties.

BACKGROUND

1. Field of the Invention

The present invention relates to a method of enhancing natural killer cell (NK cell) expansion, and a composition for culturing NK cell.

2. Discussion of Related Art

A human immune system is regulated by complicated mechanisms, and when there is an imbalance of the immune system, a variety of intractable diseases such as cancer may occur. Therefore, the development of an immune cell therapeutic agent, which is a method for resolving the imbalance occurring in the immune system so as to recover and maintain a normal condition thereof, would be desirable.

The human immune system is divided into an innate immune system and an adaptive immune system. The innate immune system consists of cells that are the first to attack a foreign antigen which has entered the human body. As representative cells, NK cells have attracted attention as a cell therapeutic agent since they are able to kill various types of cancer cells, and recognize the cancer cells without being restricted to a particular antigen.

The most important requirements for the use of immune cells as a cell therapeutic agent are a method to expand these cells to a very high number; and enrichment of cells with high anticancer activity. Also, such obtained cells should effectively survive in the body for long term following administration.

However, ex vivo-cultured immune cells do not maintain their survival for long term. In particular, as the cells proliferate, they are liable to undergo apoptosis or cellular senescence. For this reason, the effectiveness of ex vivo-cultured NK cells when administered as a therapeutic agent is dependent on maintaining stable function and persistence in the patient' body for long term.

Generally, apoptosis and cellular senescence are caused by various types of cell-mediated stress.

Reactive oxygen species (ROS) are naturally generated by the normal metabolism of oxygen, and play an important role in cell signaling and homeostasis. ROS rapidly increased under environmental stress and give rise to oxidative stress, which causes cellular apoptosis or senescence.

The ROS are typically generated by mitochondria or NADPH oxidase, and a low level of the ROS acts as an intracellular signaling molecule. However, excessive ROS may damage a macromolecule such as DNA, a protein or a lipid, ultimately resulting in cellular senescence or apoptosis.

The p53 gene is expressed in all human cells, and its role of p53 in the tumorgenesis has been reported in many studies. However, there have been no satisfactory results describing the relationship between the p53 gene and immune cells. The p53 gene is one of the tumor suppressor genes, and it has been reported that when the p53 gene mutates, causes defects in DNA repair, apoptosis, autophagy, metabolism, etc., then the normal cells become cancerous.

Today, it is known that a loss in the function of the p53 gene is found in more than 50% of cancer patients, and it is reported that proliferation of the cancer cells can be completely suppressed by injecting the p53 gene into human bladder cancer cells.

SUMMARY OF THE INVENTION

The present invention is directed to providing a method of more effectively enhancing human-derived NK cell expansion and maintaining activity of NK cells by treating the cells with a reactive oxygen species (ROS) inhibitor and/or a p53 protein inhibitor.

The present invention is also directed to providing a composition for culturing or storing NK cells, which comprises one or more selected from the group consisting of an ROS inhibitor and a p53 inhibitor as an active ingredient.

The present invention is also directed to providing a composition for treating cancer, which comprises NK cells prepared by the above-mentioned method.

To accomplish the above objects, the inventors had studied to overcome apoptosis of NK cells during ex-vivo expansion process, thereby obtaining more NK cells. The inventors hypothesized that ex-vivo NK cell expansion would be greatly enhanced in the presence of a variety of inhibitors relating to ROS and p53. Indeed, inventors found that NK culture efficiency was increased when a ROS inhibitor and/or a p53 inhibitor were included in ex-vivo culture process, thereby completing the present invention.

In one aspect, the present invention provides methods for enhancing proliferation of NK cells, which comprises treating one or more selected from the group consisting of a ROS inhibitor and a p53 inhibitor.

In another aspect, the present invention provides a composition for culturing or storing NK cells, which comprises one or more selected from the group consisting of a ROS inhibitor and a p53 inhibitor as an active ingredient.

In still another aspect, the present invention provides a pharmaceutical composition in use for preventing or treating cancer, which comprises NK cells obtained by the above-mentioned method as an active ingredient.

In yet another aspect, the present invention provides a method of treating cancer, which includes administering NK cells obtained by the above-mentioned method at an effective dose.

When natural killer (NK) cells are cultured by treating the cells with a reactive oxygen species (ROS) inhibitor and/or a p53 protein inhibitor according to the present invention, a higher cell number may be obtained than the conventional culture method without a change in the function of the cells, and thus the NK cells required for production of cell therapeutic agents may be more effectively obtained.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a graph illustrating the growth curve of NK cells cultured by a conventional culture method without the treatment of an inhibitor of the present invention. In this graph, the x axis indicates a culture day (days), and the y axis indicates a cell number ($\times 10^6$ cells);

FIG. 2 illustrates time-dependent changes in the expression of cellular senescence markers and apoptosis markers during NK cell expansion processes, without the treatment of an inhibitor according to the present invention;

FIG. 3 is a graph illustrating NK cell numbers in ex-vivo cultures in the presence or absence of apocynin treatment. Apocynin was added at three-day intervals starting at day 10 of NK cultures, to examine the influence of a ROS inhibitor on the growth of NK cells. Blue represents a control group (control), red represents an apocynin-treated group, and in the graph, the x axis indicates a culture day (days), and the y axis indicates a cell number ($\times 10^6$ cells);

FIG. 4 is a graph illustrating NK cell numbers in ex-vivo cultures in the presence or absence of trolox (50 µM) treatment, to examine the influence of ROS inhibitor on the growth of NK cells. Blue represents a control group (control), red represents a trolox-treated group, and in the graph, the x axis indicates a culture day (days), and the y axis indicates a cell number ($\times 10^6$ cells);

FIG. 5 is a graph illustrating NK cell numbers in ex-vivo cultures in the presence or absence of pifithrin treatment to examine the influence of p53 inhibitor on the growth of NK cells. Blue represents a control group (control), red represents a pifithrin-α-treated group, and in the graph, the x axis indicates a culture day (days), and the y axis indicates a cell number ($\times 10^6$ cells);

FIG. 6 is a graph illustrating NK cell numbers in ex-vivo cultures in combination of a ROS inhibitor and a p53 inhibitor on the growth of NK cells. Blue represents a control group (control), red represents a trolox and pifithrin-α-treated group, and in the graph, the x axis indicates a culture day (days), and the y axis indicates a cell number ($\times 10^6$ cells);

FIG. 7 is a graph illustrating anti-tumor activity of NK cells cultured in the absence or presence of inhibitors (apocynin, trolox, pifithrin-α, and trolox+pifithrin-α). In the graph, E:T of the x axis represents Effector (NK Cells): Targets (Tumor cells).

FIG. 8 is a graph illustrating the expression of CD107a (the index of cell killing activity) and secretion of IFN-γ (cytokine) in NK cells cultured in the presence or absence of ROS/p53 inhibitors (apocynin, trolox, pifithrin-α, and trolox+pifithrin-α).

FIG. 9 is a graph illustrating reduction of ROS in NK cells cultured with or without inhibitors; apocynin (Apo), trolox (Tro), pifithrin-α (Pi), and trolox and pifithrin-α (T+P). ROS was measured by Flow Cytometry of NK cells stained with DCF-DA.

DETAILED DESCRIPTION OF EXEMPLARY EMBODIMENTS

The present invention provides a method for enhancing proliferation of NK cells, which comprises treating NK cells with one or more selected from the group consisting of a ROS inhibitors and a p53 inhibitors; a composition in use for preventing or treating cancer, comprising NK cells obtained by the above-mentioned method; and a composition for culturing or storing NK cells, which comprises one or more selected from the group consisting of a ROS inhibitor and a p53 inhibitor as an active ingredient.

Also, the present invention provides a method of treating cancer using NK cells obtained by the above-mentioned method.

Hereinafter, configuration of the present invention will be described in detail.

The term "treatment" used herein, unless particularly mentioned otherwise, refers to all behavior involved in suppressing, alleviating or beneficially changing clinical events associated with a disease. Also, the treatment may refer to increasing survival, compared with viability expected when a disease is not treated. The treatment includes both therapeutic and preventive means.

The term "subject" used herein, unless particularly mentioned otherwise, refers to a vertebrate, preferably, a mammal such as a dog, a cat, a mouse, or a human.

The present invention provides a method for enhancing NK cell proliferation.

The method for enhancing NK cell proliferation according to the present invention may be a method of culturing NK cells to increase a yield of the NK cells, or a method of proliferating NK cells on a large scale. Also, the method according to the present invention may increase a yield of the NK cells by preventing senescence or apoptosis of the NK cells, and therefore, the method according to the present invention may present a method for suppressing the senescence or apoptosis of NK cells during ex-vivo NK cell expansion, or a storage method for maintaining the activity of proliferated or cultured NK cells.

The method for enhancing NK cell proliferation is preferably an ex-vivo expansion method.

The NK cells may be derived from a human, and are preferably human peripheral blood mononuclear cell (PBMC)-derived NK cells. The PBMC is a mononuclear cell isolated from peripheral blood generally used in anticancer immunotherapy. The PBMC may be obtained from human blood by a known method, for example, a Ficoll-Hypaque density gradient method.

PBMCs used in the present invention may be obtained from a normal person, a patient having a risk of cancer or a cancer patient, and are not necessarily autologous. Allogeneic PBMCs may also be used in induction and proliferation of NK cells for anticancer immunotherapy according to the present invention. Depending on the donor, variations exist in the absolute number and fold increase of expanded NK cells. However, all donors tested demonstrated enhanced NK cell expansion in the presence of a ROS inhibitor and/or a p53 inhibitor.

The NK cell expansion method may comprise treating one or more inhibitors selected from the group consisting of ROS inhibitors and p53 inhibitors.

In an exemplary embodiment of the present invention, the treatment may refer to culturing NK cells from PBMCs in the presence of one or more of a ROS inhibitor and a p53 inhibitor for 1 to 3 weeks. More specifically, the cells may be cultured by treatment with one or more of the inhibitors at 3-day intervals.

Therefore, the NK cell expansion method may include inducing and expanding NK cells from PBMCs; and culturing the expanded NK cells for 1 to 3 weeks in the presence of one or more inhibitor selected from the group consisting of the ROS inhibitor and the p53 inhibitor.

The ROS inhibitor refers to a substance that inhibits the generation of ROS in cells, wherein ROS are unstable oxygen-containing species generated in various metabolic processes and cause oxidation in the body and damage to a cell structure.

The ROS inhibitor has no limitation to its type as long as the generation of ROS is suppressed, and may be, specifically, one or more selected from the group consisting of 1-(4-hydroxy-3-methoxyphenyl)-ethanone (apocynin), 6-hydroxy-2,5,7,8-tetramethylchroman-2-carboxylic acid (trolox), pyrrolidine dithiocarbamate (PDTC), glutathione (GSH), catalase, manganese superoxide dismutase (Mn-SOD), vitamin E and Quercetin, and preferably any one of apocynin, trolox and a combination thereof. When NK cells are cultured in the presence of an inhibitor, apoptosis and senescence may be prevented, and cell viability may be increased, thereby increasing NK cell expansion efficiency.

Apocynin (4-hydroxy-3-methoxyacetophenone) is a substance that is first isolated from *Apocynum cannabinum*, and a compound used as an inhibitor for NADPH oxidase, an enzyme associated with ROS generation. Accordingly, it is known that when cells are treated with the apocynin, the NADPH oxidase is suppressed, resulting in the suppression of the ROS generation.

Trolox (6-hydroxy-2,5,7,8-tetramethylchroman-2-carboxylic acid) is an analog of vitamin E, which is soluble in water, and may serve to reduce oxidation stress or damage in treatment.

The p53 inhibitor does not have a limitation to its type as long as the expression of a p53 gene or protein is suppressed or inhibited, and may be, for example, one or more selected from the group consisting of 2-(2-imino-4,5,6,7-tetrahydrobenzothiazol-3-yl)-1-p-tolylethanone hydrobromide (pifithrin-α) and pifithrin-µ, and preferably, pifithrin-α. When NK cells are cultured in the presence of the p53 inhibitor, apoptosis and senescence may be prevented, and thus cell viability may be increased, thereby increasing NK cell expansion efficiency.

The pifithrin-α is a p53 inhibitor, and is generally known to adjust p53-mediated apoptosis or transcription of a p53-dependent gene (cyclin G, p21/waf1), resulting in increasing cell viability.

Also, the inhibitor may include all of the ROS inhibitors and the p53 inhibitors. As an example, trolox and pifithrin-α may be treated in a molar ratio of 50 to 150:1, and preferably 80 to 120:1. As described above, when both of the ROS inhibitor and the p53 inhibitor are treated, the culture efficiency of the NK cells may be further increased.

In an exemplary embodiment of the present invention, to examine the influence of the inhibitor on the culture of NK cells, a yield of the cells according to culture day was examined in a group in which the NK cells are treated with each of the ROS inhibitor or the p53 inhibitor or a combination of the inhibitors, compared with a group in which the NK cells are not treated with any of the inhibitors (control group), and it was experimentally confirmed that more cells are obtained in all of the inhibitor-treated groups than the control group (FIGS. 3 to 6), and it was confirmed that the NK cells obtained by the culture method have almost similar or higher cell killing activity, lower ROS production, and thus are more potent on senescence or apoptosis, compared with the conventional NK cells (FIGS. 7 to 9).

The inhibitor may be treated at 1 nM to 500 µM, based on the cell number of $2.5 \times 10^6$ cells. When the NK cells are cultured by treatment with the inhibitor as described above, a higher cell number may be obtained than the conventional culture method without a change in the function of the cells, and thus the NK cells required for production of cell therapeutic agents may be more effectively obtained.

Specifically, based on a cell number of $2.5 \times 10^6$ cells, apocynin may be treated at 100 µM to 800 µM, 200 µM to 600 µM, or 300 µM to 500 µM, trolox may be treated at 10 to 80 µM, 25 µM to 65 µM, or 35 µM to 55 µM, and pifithrin-α may be treated at 0.05 µM to 20 µM, 0.5 µM to 5 µM, or 0.7 µM to 3 µM. Also, when trolox and the pifithrin-α are treated in combination, 25 µM to 65 µM or 35 µM to 55 µM trolox and 100 nM to 800 nM or 300 nM to 600 nM pifithrin-α may be treated in combination.

The inhibitor may be treated at least once at 1-day to 10-day intervals, preferably at least once at 1-day to 5-day intervals, and more preferably at least once at 2-day to 4-day intervals. When the inhibitor is treated at the above-mentioned intervals, the toxicity of the inhibitor does not have an effect on the NK cells, and a yield after culture for proliferation may be increased.

The treatment may be performed on NK cells, a culture medium of the cells, or a culture composition.

The proliferating method may further include inducing and proliferating NK cells from PBMCs before culturing the NK cells. This step may be performed for 1 to 20 days, and preferably 8 to 12 days, and performed in vitro.

Also, the inducing and proliferating step may be co-culturing the PBMCs with feeder cells, preferably co-culturing the PBMCs with irradiated feeder cells, and more preferably co-culturing the PBMCs with feeder cells in the presence of a cytokine. The feeder cells may be any one selected from the group consisting of a Jurkat cell line, EBV-LCL and a combination thereof. When the PBMCs are co-cultured with the feeder cells, induction to the NK cells and proliferation efficiency may be further increased.

The term "Jurkat cells" or "Jurkat cell line" is a blood cancer (immortalized acute T cell leukemia) cell line, which was developed by Dr. Arthur Weiss at University of California at San Francisco. The Jurkat cells are cells capable of expressing various chemokine receptors and producing IL-2, but is a cell line which has no probability as a candidate of feeder cells for anticancer immunotherapy because an NK cell activity inhibitory factor, that is, MHC class I, is highly expressed on a surface of the cells. However, it has been known by screening a variety of blood cancer cell lines for differentiation and proliferation into NK cells from PBMCs, conducted by the inventors, that the Jurkat cells are able to be used as feeder cells (refer to Korean Patent Application No. 10-2010-0078777). The Jurkat cells used in the present invention may be provided from ATCC (ATCC TIB-152).

In the present invention, as a medium, a conventional medium that can be used in the culture of NK cells or induction and proliferation into NK cells from PBMCs may be used without limitation, and for example, RPMI, DMEM, X-VIVO10, X-VIVO20, CellGro SCGM and RPM1640 media may be used, but the present invention is not limited thereto.

In the present invention, other culture conditions are the same as conventional conditions for culturing NK cells.

Also, the present invention provides a composition for culturing NK cells, which includes one or more selected from the group consisting of an ROS inhibitor and a p53 inhibitor as an active ingredient.

In an exemplary embodiment of the present invention, it was confirmed that when NK cells are cultured using the culture composition, the cell killing activity of the cells may be improved, the apoptosis and senescence of the cells may be prevented, and thus more NK cells may be proliferated and yielded.

There is no limitation to a method for using the culture composition. For example, the culture composition may be directly treated on the NK cells, and may be mixed with a culture medium or composition for culturing the NK cells.

Unless particularly defined or limited herein, a culture medium and other culture conditions may be the same as those conventionally used.

Also, the present invention provides a composition in use for preventing or treating cancer, which includes the NK cells obtained by the method of the present invention as an active ingredient, a use of the NK cells for preparing a pharmaceutical composition in use for preventing or treating cancer, and a method of preventing and treating cancer, which includes administering the NK cells obtained by the method of the present invention or the composition including the same to a subject at an effective dose.

In an exemplary embodiment of the present invention, it was confirmed by an experiment that the NK cells obtained by the proliferating method of the present invention have a low risk of apoptosis caused by senescence because of no functional degradation in the cell killing activity of the cells and low ROS production, and thus the NK cells according to the present invention may be useful in the prevention and treatment of cancer. Particularly, the NK cells according to the present invention may be more effective for cell therapeutic agents, and in improvement of stability.

The cancer includes all types of cancer such as solid cancer, blood cancer, etc., and thus the present invention is not particularly limited thereto.

The subject may be a human in need of prevention and/or treatment of cancer, which includes a patient having a risk of cancer or a normal person, as well as the cancer patient.

The pharmaceutical composition may include an active ingredient and an active or inactive pharmaceutically acceptable carrier, which constitute a composition suitable for diagnostic or therapeutic uses in vitro, in vivo or ex vivo.

The pharmaceutical composition may be formulated by further comprising a pharmaceutically acceptable carrier.

The "pharmaceutically acceptable carrier" refers to a carrier or a diluent, which does not inhibit biological activity and properties of an administered ingredient without considerably stimulating a biological organism. The pharmaceutically acceptable carrier in the present invention may be saline, sterilized water, Ringer's solution, buffered saline, a dextrose solution, a maltodextrin solution, glycerol, ethanol, and a mixture of one or more thereof. When necessary, the pharmaceutically acceptable carrier may be formulated in the form of a suitable injection to be injected into tissue or an organ by adding a conventional additive such as an antioxidant, a buffer or a bacteriostat. Also, the pharmaceutically acceptable carrier may be formulated as a dry product (particularly, a lyophilized dry product) capable of being an injectable solution by adding an isotonic sterilized solution, or sterilized solution or saline, depending on a case. The pharmaceutically acceptable carrier may be prepared by suspending the NK cells in an aqueous solution containing a suitable ingredient at a suitable concentration as necessary.

Also, the composition of the present invention preferably further includes a filler, an excipient, a dispersant, a binder, and a lubricant. Also, the composition of the present invention may be formulated by a method known in the art to provide instant, suspended or delayed release of the active ingredient after being administered to a mammal.

The term "administration" used herein refers to introduction of the composition of the present invention to a patient by a suitable method. The composition of the present invention may be administered by various routes such as oral or parenteral routes that can reach target tissue. The composition of the present invention may be administered by intraperitoneal administrate, intravenous administration, intraarterial administration, intramuscular administration, subcutaneous administration, intracutaneous administration, oral administration, local administration, intranasal administration, intrapulmonary administration, or rectal administration, but the present invention is not limited thereto.

The effective dose refers to an amount necessary to delay occurrence or progression of a specific disease to be treated, arrest the disease or have a therapeutic effect. The composition of the present invention may be administered at a pharmaceutically effective dose. It is obvious to those of ordinary skill in the art that a suitable dose per day can be determined by a clinician based on sound medical judgment. In terms of the objects of the present invention, a specific therapeutically effective dose for a specific patient may be determined according to various factors such as the type and degree of a reaction to be achieved, a specific type of a disease which uses a different agent by case, severity, types and contents of different ingredients contained in the composition, a patient's age, weight, general health condition, sex and diet, administration time, an administration route, and a secretion rate of the composition, the duration of treatment, a drug used along with or simultaneously used with a specific composition, and similar factors well known in medical fields. As an example, for adults, the PBMC-derived NK cells of the present invention may be administered at a dose of $1\times10^6$ cells/kg to $1\times10^{11}$ cells/kg, for example, $1\times10^6$ cells/kg to $1\times10^8$ cells/kg, one to several times per day, but the present invention is not limited thereto.

Hereinafter, the present invention will be described in detail with reference to examples. However, the following examples are provided to merely exemplify the present invention, and thus the scope of the present invention is not limited thereto.

EXAMPLES

Preparation Example 1: Preparation and Culture of NK Cells

Human blood was prepared, and subjected to centrifugation at 2500 rpm for 30 minutes using Ficoll (Ficoll-Paque™ PLUS, GE Healthcare). Then, peripheral blood mononuclear cells were isolated from a buffy coat.

Afterward, a Jurkat cell line irradiated at 100 Gy and an EBV-LCL cell line were co-cultured with PBMCs:KL-1: EBV-LCL in a ratio of 1:0.5:0.5 in hRPMI medium prepared by adding 10% FBS and 1% penicillin/streptomycin to RPMI1640 medium in the presence of 500 U/ml IL-2, and the medium was exchanged with hRPMI medium supplemented with 500 U/ml IL-2 once for 2 to 3 days.

Experimental Example 1: Examination of Influence of ROS and/or p53 Inhibitor on Culture of NK Cells An examination of a change of proteins expression of NK cells during the culture of the NK cell as in the Preparation Example 1 was conducted. A cell cycle-associated marker pRb, cellular senescence markers P53 and P21, ER stress markers Bip and CHOP, a DNA damage marker γH2AX, and apoptosis markers PARP and cl-caspase-7 were identified.

The results are shown in FIG. 2, confirming that most of the markers peaked at 13 to 16 days.

To examine the influence of an ROS inhibitor on NK cells, the NK cells were cultured for 10 days under the conditions of Preparation Example 1. Then, 400 μM of an apocynin (Calbiochem), 50 μM of trolox (Santa Cruz) and 1

μM of pifithrin-α (Santa Cruz) were treated individually, and 50 μM trolox and 500 nM pifithrin-α were treated in a combination. The inhibitor was treated at three-day intervals, and a cell number was assessed after culture for 2 weeks. Here, the medium was exchanged with hRPMI medium added with 500 U/ml of IL-2 once for three days, and a cell number was calculated using a hemocytometer. The number of the cells treated with or without the inhibitor was compared, and the results are shown in FIGS. 3 to 6.

As shown in FIGS. 3 and 4, in the groups treated with an ROS inhibitor such as apocynin, or the trolox, compared with the control group, the NK cell number showed a statistically significant increase. And as shown in FIG. 5, when the p53 inhibitor, pifithrin-α, was treated, compared with the control group, the NK cell number showed a statistically significant increase.

Also, as shown in FIG. 6, in the group treated with 50 μM trolox and 500 nM pifithrin-α in combination, compared with the control group, the NK cell number showed a statistically significant increase.

Experimental Example 2: Measurement of Changes in Cancer Cell Killing Activity of NK Cells An experiment was performed to examine cancer cell killing activity of NK cells treated with the inhibitor.

As target cells, K562 and A375 cells were prepared, labeled with chromium for 1 hour, co-cultured with the NK cells in a suitable ratio, and then a supernatant was taken from the cell culture after 4 hours so as to measure an isotopic value using a gamma counter. The experiment was performed on a control group which was not treated, and groups treated with apocynin, trolox, pifithrin-α and trolox+pifithrin-α, respectively, and the results are shown in FIG. 7.

As shown in FIG. 7, even when the cells were cultured with the ROS inhibitor and/or p53 inhibitor according to the present invention, the cancer cell killing activity was maintained at the same level as that in the non-treated control group.

Also, as target cells, K562 and A375 cells were prepared, and NK cells and the target cells were mixed in a ratio of 1:1 and cultured at 37° C. for 1 hour. The cell culture was added with 2.5 μl of FITC-labeled anti CD107a mAb and Golgi stop (BD Pharmingen), and further cultured at 37° C. for 5 hours. After the culture, Percp-labeled CD3 mAb, APC-labeled CD56mAb was added, followed by reaction at 4° C. for 20 minutes. For intracellular FACS, the cells were washed with FACS buffer, fixed, and stained with PE-labeled IFN-g mAb using a BD cytoperm/cytofix kit (BD Pharmingen, San Diego, Calif.), followed by flow cytometry. The experiment was performed on a control group which was not treated, and experimental groups treated with apocynin, trolox, pifithrin-α and trolox+pifithrin-α, respectively, and the results are shown in FIG. 8.

As shown in FIG. 8, even when the cells were cultured with the ROS inhibitor and/or p53 inhibitor, maintenance of the cell killing activity of the NK cells were experimentally confirmed without decreases in the expression of CD107a (marker of cell killing activity) and secretion of IFN-g (cytokine) in the NK cells.

Experimental Example 3: Measurement of ROS Generation

To measure ROS generated in in vitro-expanded NK cells, NK cells cultured by treatment with an inhibitor individually or in combination were harvested. $1 \times 10^6$ cells were seeded per well in a 24-well plate, cultured in a 5% $CO_2$ incubator for 30 minutes, and then collected. The cells were washed once with 1 ml of PBS, followed by flow cytometry using 100 μM DCF-DA. The experiment was performed on a control group which was not treated, and experimental groups treated with apocynin, trolox, pifithrin-α and trolox+pifithrin-α, respectively, and the results are shown in FIG. 9.

As shown in FIG. 9, in the trolox-treated group, compared with the control group, ROS generation was significantly decreased, and the ROS generation were gradually decreased in the order of trolox<pifithrin-α<trolox+pifithrin-α<apocynin<control group (non-treated).

Therefore, when the cells were treated with a inhibitor of the present invention, more cells may be yielded than the conventional culture methods, and moreover, in the cells cultured according to the present invention, the ROS generation was decreased, and the cell killing activity was maintained, resulting in increased functionality. Thus, it was experimentally confirmed that the cells can be effectively used as cell therapeutic agents in use for preventing or treating cancer.

By a method of proliferating NK cells on a large scale according to the present invention, when NK cells are cultured by treatment with an ROS inhibitor and/or a p53 inhibitor, a higher NK cell number can be achieved than a conventional culture method without loss in a function of the NK cells, and thus the NK cells used for cell therapeutic agents, kits, etc. can be effectively produced and obtained.

The invention claimed is:

1. A method of enhancing NK cell expansion, comprising: treating natural killer (NK) cells with a p53 inhibitor; or a reactive oxygen species (ROS) inhibitor and a p53 inhibitor, wherein the p53 inhibitor is one or more selected from the group consisting of 2-(2-imino-4,5,6,7-tetrahydrobenzothiazol-3-yl)-1-p-tolylethanone hydrobromide (pifithrin-α) and pifithrin-μ.

2. The method of claim 1, wherein NK cells are derived from human peripheral blood mononuclear cells (PBMCs).

3. The method of claim 1, wherein the ROS inhibitor is one or more selected from the group consisting of 1-(4-hydroxy-3-methoxyphenyl)-ethanone (apocynin), 6-hydroxy-2,5,7,8-tetramethylchroman-2-carboxylic acid (trolox), pyrrolidine dithiocarbamate (PDTC), glutathione (GSH), catalase, manganese superoxide dismutase (Mn-SOD), vitamin E, and Quercetin.

4. The method of claim 1, wherein the inhibitors include trolox and pifithrin-α in a molar ratio of 50 to 150:1.

5. The method of claim 1, wherein the treatment includes culturing NK cells expanded from PBMCs for 1 to 3 weeks in the presence of the p53 inhibitor; or the ROS inhibitor and the p53 inhibitor.

6. The method of claim 1, wherein the method comprises: inducing and expanding NK cells from PBMCs; and culturing the expanded NK cells for 1 to 3 weeks in the presence of the p53 inhibitor; or the ROS inhibitor and the p53 inhibitor.

* * * * *